US006876128B2

(12) United States Patent
Nguyen

(10) Patent No.: US 6,876,128 B2
(45) Date of Patent: Apr. 5, 2005

(54) SHORT-CIRCUIT NOISE ABATEMENT DEVICE AND METHOD FOR A GAS ULTRASONIC TRANSDUCER

(75) Inventor: Toan Huu Nguyen, Needham, MA (US)

(73) Assignee: General Electric Company, Schenectady, NY (US)

( * ) Notice: Subject to any disclaimer, the term of this patent is extended or adjusted under 35 U.S.C. 154(b) by 104 days.

(21) Appl. No.: 10/614,897

(22) Filed: Jul. 9, 2003

(65) Prior Publication Data

US 2005/0006985 A1 Jan. 13, 2005

(51) Int. Cl.[7] ............................................... H01L 41/08
(52) U.S. Cl. ......................... 310/325; 310/336; 73/644
(58) Field of Search ................................ 310/325, 334, 310/336; 73/644, 861.18, 861.25–861.29

(56) References Cited

U.S. PATENT DOCUMENTS

| | | | |
|---|---|---|---|
| 4,004,461 A | | 1/1977 | Lynnworth |
| 4,308,754 A | | 1/1982 | Pedersen et al. |
| 4,596,133 A | | 6/1986 | Smalling et al. |
| 4,712,428 A | * | 12/1987 | Ishii et al. ............... 73/644 |
| 4,754,650 A | | 7/1988 | Smalling et al. |
| 4,783,997 A | | 11/1988 | Lynnworth |
| 4,856,321 A | | 8/1989 | Smalling et al. |
| 4,918,990 A | | 4/1990 | Fowler et al. |
| 5,179,862 A | | 1/1993 | Lynnworth |
| 5,437,194 A | | 8/1995 | Lynnworth |
| 5,460,047 A | | 10/1995 | Jacobson |
| 5,515,733 A | | 5/1996 | Lynnworth |
| 6,047,602 A | | 4/2000 | Lynnworth |
| 6,343,511 B1 | | 2/2002 | Lynnworth et al. |
| 6,349,599 B1 | | 2/2002 | Lynnworth et al. |
| 6,575,044 B1 | | 6/2003 | Feller |

OTHER PUBLICATIONS

"Nonintrusive Flow–Measurement System", John F. Kennedy Space Center, Fla; www.nasatech.com/Briefs/Jan00, pp. 1–2, (Jan. 2000).
"Ultrasonic Flowmeters: Types of Ultrasonic Flow Meters", www.flowmeters.f2s.com/article.htm, pp. 1–4 (Copyright 2002 EESIFLO)).
"The Performance of Transit Time Flowmeters In Heated Gas Mixtures", John D. Wright, presented at 1998 ASME Fluids Engineering Division Summer Meeting, Jun. 21–23, 1998 Washington DC, pp. 1–7.
"Exciting New Flowmeter Technology Breakthrough From Panametrics—Introducing the Digitalflow™ GC868", Panametrics, pp. 1–5. (2001).
"A Clamp–On Ultrasonic Flowmeter for Gases", Michael J. Scelzo, Flow Control magazine, pp. 1–3 (Copyright 2001).
"DigitalFlow™GC868 Gas Flowmeter Clamp–On Ultrasonic Flowmeter for Gases", Panametrics, pp. 1–8 (Copyright Apr. 2002).
"CEM68 for Continuous Emissions Monitoring Systems", Panametrics, pp. 1–4 (Copyright Apr. 2002).

* cited by examiner

Primary Examiner—Mark Budd
(74) Attorney, Agent, or Firm—Nixon & Vanderhye, P.C.

(57) ABSTRACT

A vibration attenuator, for an ultrasonic transducer having a transducer shaft, having: a compressible sleeve mountable on said shaft wherein said sleeve comprises vibration attenuating material; a housing for said sleeve mountable on the shaft, and a compression device attachable to the housing and for compressing the sleeve, wherein the sleeve snugly abuts against said shaft when compressed.

20 Claims, 2 Drawing Sheets

SHORT-CIRCUIT NOISE ABATEMENT DEVICE AND METHOD FOR A GAS ULTRASONIC TRANSDUCER

BACKGROUND OF THE INVENTION

Ultrasonic flow meters typically have a pair of transducers which makes a direct contact with the process fluid. This type of flow meter configuration is referred to as "wetted" application. Each transducer is mounted on a transducer holder which is attached to a nozzle or port of a pipe or other flow channel (collectively referred to here as a "flow cell"). Flow meters transmit ultrasonic pulses into the flow cell and through the flow stream passing through the flow cell. The flow stream affects the transmitted pulses by, for example, altering the travel time of the pulses between a transmitter and receiver. By measuring the effect on the received pulses the flow meters can determine the flow rate of the stream.

Ultrasonic transit time flow meters generally have dual transducers that both emit and receive ultrasonic signal pulses. The dual transducers include an upstream transducer and a downstream transducer which are positioned such that the ultrasonic signal pulse or beam is at an inclined angle with respect to the axis of the flow cell. The upstream transducer emits an ultrasonic signal pulse that propagates through the flow cell and flow stream in a generally downstream direction. The signal pulse is received by the downstream transducer. In addition, the downstream transducer emits an ultrasonic pulse in an upstream direction that is received by the upstream transducer. The flow meter determines the difference in travel time between the ultrasonic pulses passing in a downstream direction and those passing in an upstream direction. The difference in pulse travel time can be used to determine the rate of the flow stream.

The transducer receives ultrasonic pulses and generates an electrical signal indicative of when the pulses are received. The transducer may convert to electrical signals only those pulses having a frequency similar to that of the transmitted pulse. The ultrasonic signals received by the receiving transducer includes the pulses that were originally emitted by the transmitting transducer. The received signals also include ultrasonic noise, so-called "acoustic short-circuit" noise, which consists of unwanted non-fluid-borne signals having a frequency within the range of frequency that the transducer detects. Short circuit noise typically arises from vibrations generated by the transmitting transducer and imparted or coupled mechanically to the transducer support and/or flowcell. These vibrations travel from the transmitting transducer by way of transducer shafts, transducer holders, transducer nozzles and the metal wall of the flow cell. These vibrations may have the same frequency as do the ultrasonic pulses that are transmitted through the fluid flow stream. However, these vibrations "short-circuit" the fluid flow by passing through the solid structures associated with the transducer and flow cell wall, and do not pass through the flow stream. Short circuit vibrations that are received by the transducer contribute to electrical signal noise in the measuring system. Short circuit noise interferes with achieving high accuracy and may obscure the data from the received signals from the ultrasonic pulses that pass through the flow stream.

To detect fluid flow through a pipe, ultrasonic flow meters typically use acoustic waves or vibrations having a frequency greater than 20 kHz (kilohertz). These flow meters preferably have a high SNR (signal-to-noise ratio) of greater than 20 decibels (dB). A high SNR promotes reliable signal detection, robust performance of the flow meter, and accurate readings of the flow rate by the flow meter. Conventional transit-time ultrasonic flow meters have attainted SNRs of greater than 20 dB for most liquid flow applications and in some high pressure gas flow applications. The SNRs tend to be low, e.g. less than 10 dB, for conventional transit-time ultrasonic flow meters measuring: low pressure gas flows, e.g. atmospheric flows; gases at high flow rates; high temperature gas flows that require transducers tolerant of high temperatures, and gas flows including saturated steam with condensed water. Accordingly, there is a long felt need for transit-time ultrasonic flow meters that have high SNRs when sensing gas flows having low pressures, high gas temperatures, high gas flow rates, and gas flows having saturated steam.

BRIEF DESCRIPTION OF THE INVENTION

In a first embodiment, the invention is a vibration attenuator for an ultrasonic transducer having a transducer shaft, said attenuator comprising: a compressible sleeve mountable on said shaft wherein said sleeve comprises vibration attenuating material; a housing for said sleeve mountable on said shaft, and a compression device attachable to said housing and for compressing said sleeve, wherein said sleeve snugly abuts against said shaft when compressed.

In a second embodiment, the invention is a vibration attenuator for an ultrasonic transducer having a shaft, said dampening device comprising: a cylindrical housing having an internal cylindrical surface, an closed end with an aperture and an open end opposite to the closed end, wherein said internal cylindrical surface has a screw thread adjacent the open end; a plurality of compressible rings arranged in a stack within the internal cylindrical surface of the housing, wherein said rings are coaxial with the housing, and a screw plug having a screw thread to screw into the screw thread of the housing, an end which abuts against the stack of rings in the housing, and a conduit coaxial with the housing and rings, wherein the plug compresses the stack of ring as the plug screws into the housing, wherein the transducer shaft extends through the housing, rings and plug, and the rings fit snugly against the shaft when the rings are compressed in the housing.

In a third embodiment, the invention is a method of attenuating vibration in an ultrasonic instrument having an ultrasonic transducer and a transducer shaft, said method comprising: clamping a sleeve of compressible material around the shaft, and attenuating ultrasonic vibrations travelling through the shaft by dampening the vibration with the sleeve.

DETAILED DESCRIPTION OF THE INVENTION

Figure 1:
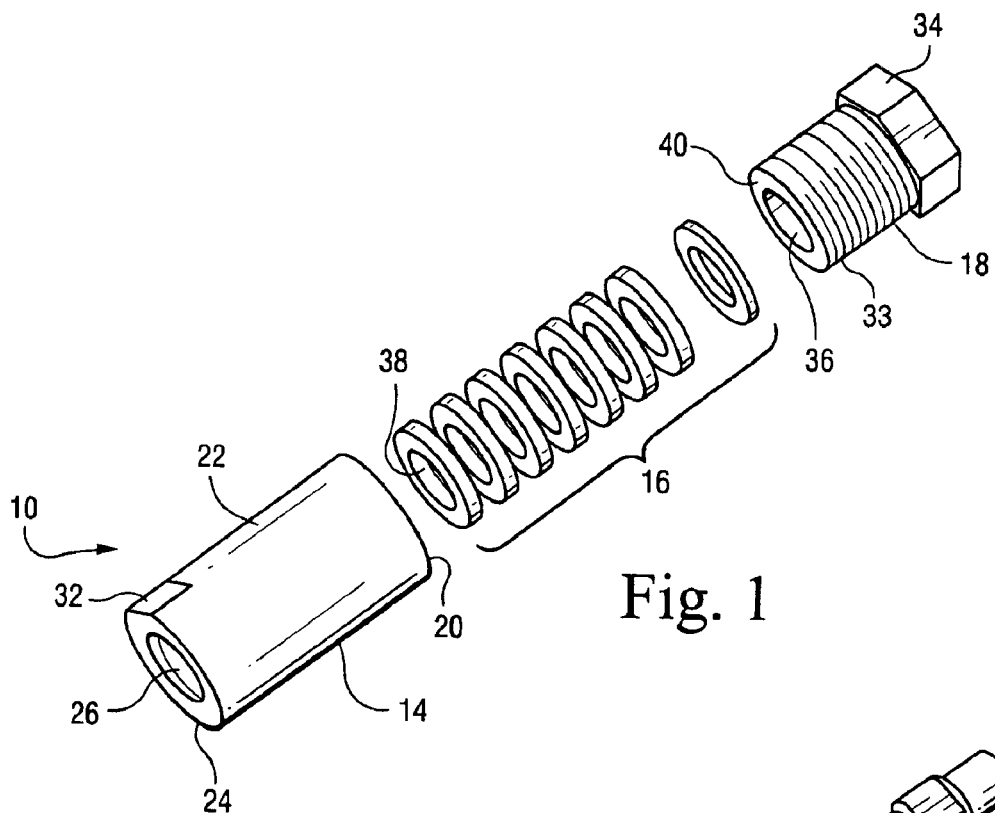
FIG. 1 is an exploded view of an dampening mechanism the present invention.
Figure 2:
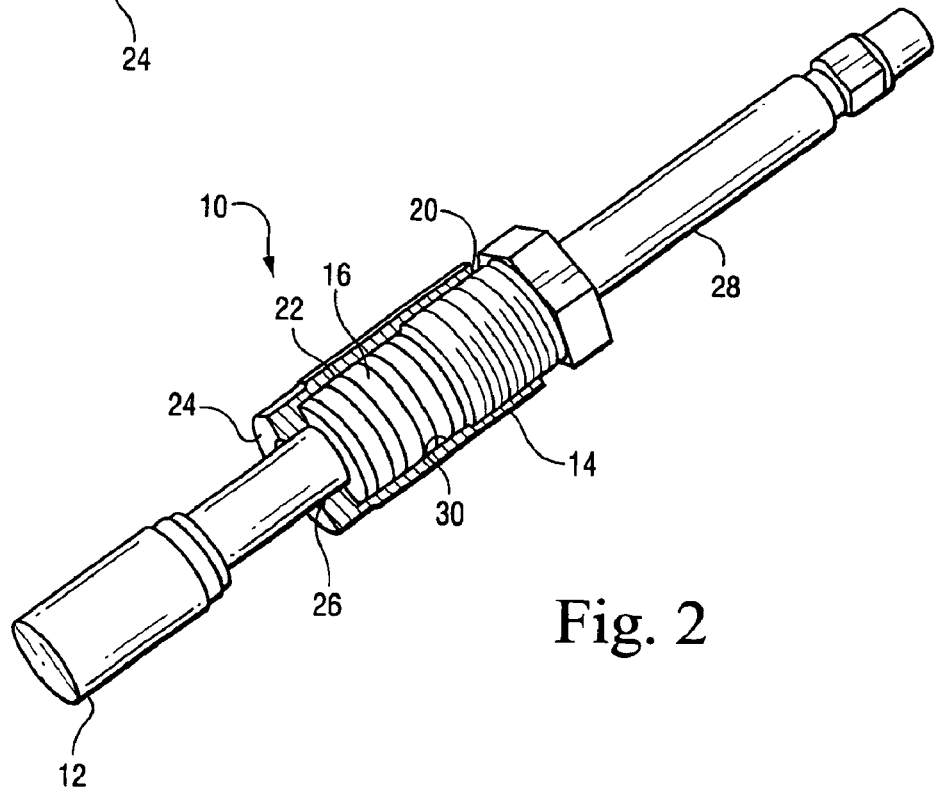
FIG. 2 is a perspective view of the embodiment shown in FIG. 1 in an assembled state.

FIGS. 1 and 2 show an exploded view and an assembled view, respectively, of a dampening mechanism 10 for mounting as a sleeve on the shaft 28 of an ultrasonic gas transducer 12. The dampening mechanism includes a stand-alone, cylindrical housing 14, a stack of damping rings 16 and a plug screw 18 to hold the rings in the housing. The plug screw fits into an open end 20 of the housing, which has an internal thread to receive the plug.

The cylindrical housing 14 has cylindrical wall 22, and a closed end 24, opposite to the open end, with an aperture 26 to slidably receive the transducer shaft 28. The interior surface 30 of the annular wall 22 of the housing may be a relatively smooth cylindrical surface, except for the threaded surface adjacent the open end 20 of the housing. The interior wall surface 30 has a constant diameter of about the same as or slightly larger than the diameter of the rings 16. The cylindrical wall 30 provides a snug fit around the perimeter of the rings 16, when the rings are compressed in the housing. The cylindrical housing 14 may have a pair of outer flat surfaces 32 to receive a wrench used to tighten the screw plug 18 in the housing 14.

The plug 18 may be a cylinder with a threaded outer surface 33 which mates with the interior threaded surface adjacent the open end 20 of the cylindrical housing 14. The plug may also have a hexagonal cap 34 which provides a grip for a tightening wrench. The depth to which the plug is screwed into the housing 14 depends on the amount of compression to be applied to the rings 16. The screw plug 18 has an axial conduit 36 to slidably receive the transducer shaft.

A plurality rings 16, such as seven, are stacked in the cylindrical housing. Each ring is an annulus having an outside diameter approximately the same as the interior diameter of the interior wall 30 of the housing 14. The rings have an inner circular diameter slightly larger than the outer diameter of the transducer shaft. The rings are deformable and may be formed of a packing material, such as a pre-formed stack of 9000 EVSP Simplified manufactured by Garlock of Palmyra, N.Y. The rings may also be formed of other valve stem packing materials, a rope material helically arranged in the housing, or other deformable materials that provide high frequency vibration absorption and dampening.

The dampening mechanism may comprise a stand-alone housing, a threaded plug and a stack of damping rings 16. The damping rings abate the vibration noise. The rings may be a pre-formed stack of packing material or a valve stem rope material helically arranged or cut and formed in rings 16 in the housing 20. The rings 16, when compressed axially inside the housing 20, expand radially inward and squeeze tightly around the transducer shaft 28. The vibration noise abatement in the transducer shaft is realized by the squeezing action of the packing material on the transducer shaft.

As shown in FIG. 2, the dampening mechanism 10 is assembled by stacking the rings 16 in the cylindrical housing 14 such that the interior apertures 38 of the rings are coaxial with the cylindrical housing 14. The transducer shaft 28 is also coaxial with the housing and extends through the housing, rings and the plug. The shaft 28 is inserted into the housing and through the packing material 16 before the plug is tightened on the housing.

As the plug 18 screws into the housing 14, the end 40 of the plug compresses the rings 16 in the housing. As the rings compress, they expand radially inward and squeeze tightly around the transducer shaft. Packing gland material is conventionally compressed by thirty percent (30%). Applying such compression to the ring stack, the length of the compressed stack of rings is approximately seventy percent (70%) of the uncompressed length of the stack. For example, a ring stack having a one inch (2.54 cm) uncompressed length will be compressed to 0.7 inches (1.8 cm). Accordingly, the length of the screw threads 33 on the plugs should be sufficient, e.g., 0.5 inches (1.25)cm, to apply the desired amount of compression to the ring stack.

The dampening mechanism 10 may be a stand-alone sleeve mounted on the transducer shaft 28. The mechanism may be unconnected to any structure other than the transducer shaft. In a dual transducer flow meter, a dampening mechanism 10 may be mounted on one or both transducer shafts.

The snug fit between the rings 16 and transducer shaft 28 allows the rings to dampen the vibration travelling through the shaft. The rings 16 attenuate the vibration travelling from a transmitting transducer, through the transducer shaft 28 and to the receiving transducer. By dampening vibrations in the transducer shaft, the vibrations travelling from the shaft to the walls of the flow cell are reduced. If the dampening mechanism 10 is applied to both shafts of a dual transducer flow meter, then the mechanism 10 on the shaft 28 of the transmitting transducer will attenuate short circuit noise before the noise is imparted to the flow cell wall. The mechanism 10 on a shaft 28 of the receiving transducer will dampen vibrations traveling from the flow cell wall to the receiving transducer. If the dampening mechanism 10 is applied to only one shaft, then it will still attenuate short circuit noise—although less so than if two dampening mechanisms were present The dampening mechanism may be applied to: gas and liquid ultrasonic flowmeters; contrapropagation vibration attenuators; other ultrasonic transducers used for non-destructive testing; acoustic level detection instruments, and other vibration sensitive devices operating in high temperature applications. The components of the dampening mechanism may be tolerant of high temperatures, such as 500° F.

Figure 3:
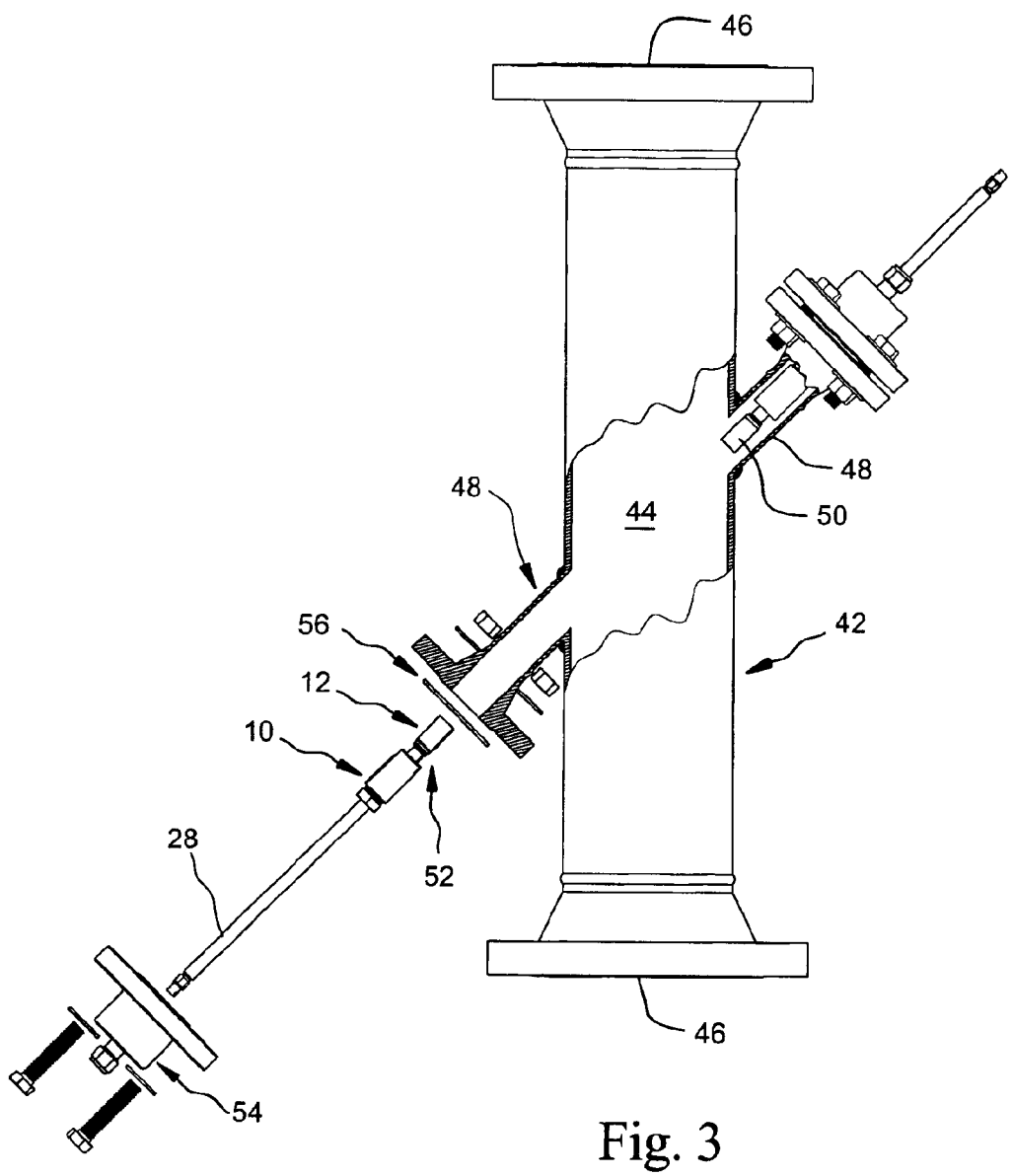
FIG. 3 is side view of a flowcell, shown partially cutaway, having a pair of noise-abated transducers each with a dampening mechanism.

FIG. 3 shows a flowcell 42 having a cylindrical flow path 44 which is internal to the cell and has inlet and outlet ports 46 at opposite ends of the path of the flow cell. The flow cell has a pair of transducer nozzle mounts 48 on opposite sides of the path 44. The nozzle mounts are arranged at an angle to the path so that an upstream transducer 50 is upstream of a downstream transducer 52. The upstream transducer is shown mounted in the nozzle mount 48. The downstream tranducer is shown in an exploded view, to better illustrate the transducer 12, dampening mechanism 10 and shaft 28, which are held in the nozzle by a transducer holder 54 which attaches as an end cap to an end of the nozzle mount 48. A gasket 56 provides a seal between the transducer holder and the nozzle mount.

The dampening mechanism 10 is externally mounted on the shaft of the transmitting transducer to abate vibration noise propagating on the transducer shaft from the transducer head 12 to the transducer holder 54. Similarly, the dampening mechanism 10 is externally mounted on the shaft of the receiving transducer to abate the vibration noise propagating on the transducer shaft from the transducer holder to the transducer head.

The dampening mechanism 10 is a short-circuit noise abatement device applicable to, for example, a gas ultrasonic transducer 12. The mechanism 10 includes a stand-alone cylindrical housing 20, a sleeve of damping rings 16 and a threaded plug 18, all of which having internal diameters for receiving the transducer shaft. As the threaded plug screws into the cylindrical housing, the sleeve of damping rings 16 is compressed. As the rings compress, they expand radially inward and squeeze tightly around the transducer shaft 28. As a result, the vibration noise in the transducer shaft is abated. This short-circuit noise abatement device can be applied on the shaft of the transmitting and/or the receiving transducers. For optimum result a dampening mechanism should be applied to both transducer shafts, one on the transmitting transducer and the other on the receiving transducer.

A pair of dampening mechanisms 10 were applied to both transducer shafts in a dual transducer transit time ultrasonic flow meter. The presence of the dampening mechanisms increased the SNR of the flowmeter by more than 5.3 dB. In particular, the flow meter with dampening mechanisms 10 had an SNR of 22.5 dB and had an SNR of only 17.2 dB without the mechanisms. The test conditions included a gas flow at atmospheric pressure (0 psig) and at room temperature. Increasing the SNR by 5.3 dB nearly doubled the transducer output voltage ratio of actual signal verses noise.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A vibration attenuator for an ultrasonic transducer having a transducer shaft, said attenuator comprising:
    a compressible sleeve mountable on said shaft wherein said sleeve comprises vibration attenuating material;
    a housing for said sleeve mountable on said shaft, and
    a compression device attachable to said housing and for compressing said sleeve, wherein said sleeve snugly abuts against said shaft when compressed.

2. A vibration attenuator as in claim 1 wherein said sleeve is formed of a stack of deformable rings.

3. A vibration attenuator as in claim 1 wherein said housing is a cylinder having an internal cylindrical wall having a diameter to accommodate the sleeve.

4. A vibration attenuator as in claim 1 wherein said housing is a cylinder having an open end with an internal screw surface, and said compression device is a screw plug which screws into the open end and screw surface of the housing.

5. A vibration attenuator as in claim 1 wherein said deformable material is a valve stem packing material.

6. A vibration attenuator as in claim 1 wherein said housing, compressible sleeve, compression device are each coaxial with said shaft.

7. A vibration attenuator for an ultrasonic transducer having a shaft, said dampening device comprising:
    a cylindrical housing having an internal cylindrical surface, an closed end with an aperture and an open end opposite to the closed end, wherein said internal cylindrical surface has a screw thread adjacent the open end;
    a plurality of compressible rings arranged in a stack within the internal cylindrical surface of the housing, wherein said rings are coaxial with the housing, and
    a screw plug having a screw thread to screw into the screw thread of the housing, an end which abuts against the stack of rings in the housing, and a conduit coaxial with the housing and rings, wherein the plug compresses the stack of ring as the plug screws into the housing,
    wherein the transducer shaft extends through the housing, rings and plug, and the rings fit snugly against the shaft when the rings are compressed in the housing.

8. A vibration dampening as in claim 7 wherein said rings are formed of a valve stem packing material.

9. A vibration attenuator as in claim 7 wherein said housing, rings, plug are each coaxial with said shaft.

10. A vibration attenuator as in claim 7 wherein the plug is extendable into the housing so as to compress the stack at least thirty percent of an uncompressed length of the stack.

11. A method of attenuating vibration in an ultrasonic instrument having an ultrasonic transducer and a transducer shaft, said method comprising:
    a. clamping a sleeve of compressible material around the shaft, and
    b. attenuating ultrasonic vibrations travelling through the shaft by dampening the vibration with the sleeve.

12. A method as in claim 11 wherein the compressible material is clamped around the shaft by housing the material in a cylindrical housing and compressing the material within the housing so that the material expands radially inward against the shaft.

13. A method as in claim 12 wherein the compressible material is compressed by a plug which is screwed into one end of the housing.

14. A method as in claim 13 wherein the compressible material is compressed at least thirty percent of an uncompressed length of the material.

15. A method as in claim 11 wherein the compressible material is clamped to a shaft of a transmitting transducer.

16. A method as in claim 11 wherein the compressible material is clamped to a shaft of a receiving transducer and a second sleeve of compressible material is clamped to a shaft of a transmitting transducer.

17. A method as in claim 16 wherein the receiving transducer and transmitting transducer are components of a transit time ultrasonic flow meter.

18. A method as in claim 17 wherein the flow meter has a signal to noise ratio (SNR) of at least 20.

19. A method as in claim 11 wherein the attenuated ultrasonic vibrations are of a frequency of at least 20 kHz.

20. A method as in claim 11 wherein the compressible material encircles the shaft.

* * * * *